(12) United States Patent
Patel et al.

(10) Patent No.: US 7,977,289 B2
(45) Date of Patent: * Jul. 12, 2011

(54) SUBSTANTIALLY SURFACTANT FREE IN-SHOWER GEL COMPOSITIONS COMPRISING HYDROPHILIC AND HYDROPHOBIC BENEFIT AGENTS

(75) Inventors: Rajesh Patel, Middlebury, CT (US); Evan Charles Murphy, Oakville, CT (US); Rosa Mercedes Paredes, Shelton, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 169 days.

This patent is subject to a terminal disclaimer.

(21) Appl. No.: 12/115,816

(22) Filed: May 6, 2008

(65) Prior Publication Data

US 2009/0281013 A1 Nov. 12, 2009

(51) Int. Cl.
A61K 7/50 (2006.01)

(52) U.S. Cl. ........ 510/130; 510/137; 510/159; 424/70.1

(58) Field of Classification Search .................. None
See application file for complete search history.

(56) References Cited

U.S. PATENT DOCUMENTS

| | | | |
|---|---|---|---|
| 5,427,704 A | 6/1995 | Lawate |
| 5,472,728 A | 12/1995 | Miller et al. |
| 5,490,995 A | 2/1996 | Corrigan |
| 5,578,299 A | 11/1996 | Starch |
| 5,888,492 A | 3/1999 | Starch |
| 5,928,632 A | 7/1999 | Reusch |
| 6,156,369 A | 12/2000 | Eger et al. |
| 6,645,511 B2 | 11/2003 | Aronson et al. |
| 6,699,488 B2 | 3/2004 | Deckner et al. |
| 6,716,440 B2 | 4/2004 | Aronson et al. |
| 6,780,826 B2 | 8/2004 | Zhang et al. |
| 6,903,057 B1 | 6/2005 | Tsaur |
| 6,998,382 B2 | 2/2006 | Yang et al. |
| 2004/0223992 A1 | 11/2004 | Clapp et al. |
| 2007/0032393 A1 | 2/2007 | Patel et al. |

FOREIGN PATENT DOCUMENTS

| | | |
|---|---|---|
| DE | 197 39 447 A1 | 3/1999 |
| EP | 398 409 | 11/1990 |
| EP | 1 287 811 A2 | 3/2003 |
| WO | WO2007017118 * | 2/2007 |

OTHER PUBLICATIONS

Co-pending application: U.S. Appl. No. 11/748,943, filed May 15, 2007 to Patel et al.
Co-pending application: U.S. Appl. No. 11/850,144, filed Sep. 5, 2007 to Patel et al.
Co-pending application: U.S. Appl. No. 12/102,210, filed Apr. 14, 2008 to Patel et al.
Co-pending application: U.S. Appl. No. 12/115,841, filed May 6, 2008 to Patel et al.
"Emulsifier-free emulsion-based rinse-off formulations", Research Disclosure, Mason Publication, Hampshire, GB, vol. 483, No. 30, 483030, Jul. 2004, XP007134016, (Disclosed Anonymously).

* cited by examiner

*Primary Examiner* — Necholus Ogden, Jr.
(74) *Attorney, Agent, or Firm* — Ronald A. Koatz

(57) ABSTRACT

The invention relates to substantially surfactant free gel compositions comprising hydrophobic and hydrophilic benefit agents. Unexpectedly, the applicants have found these agents deposit with greater substantivity from such liquid gel compositions relative to surfactant-containing lotion.

11 Claims, 4 Drawing Sheets

TRICLOCARBAN RECOVERY FROM PIG SKIN AFTER TREATMENT WITH ISL PROTOTYPES (30 SECS CONTACT TIME)

TRICLOCARBAN RECOVERY FROM PIG SKIN AFTER TREATMENT WITH ISL PROTOTYPES (30 SECS CONTACT TIME)

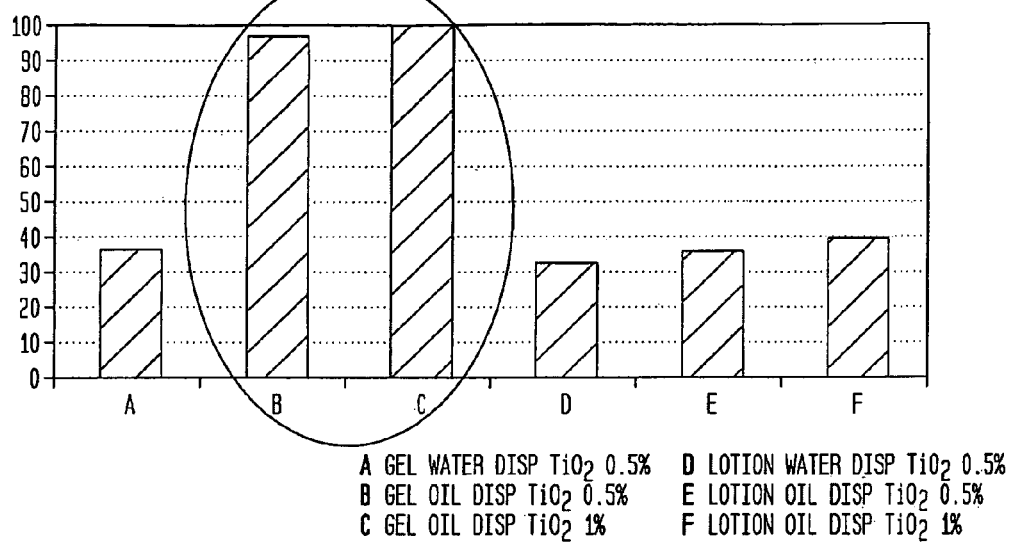
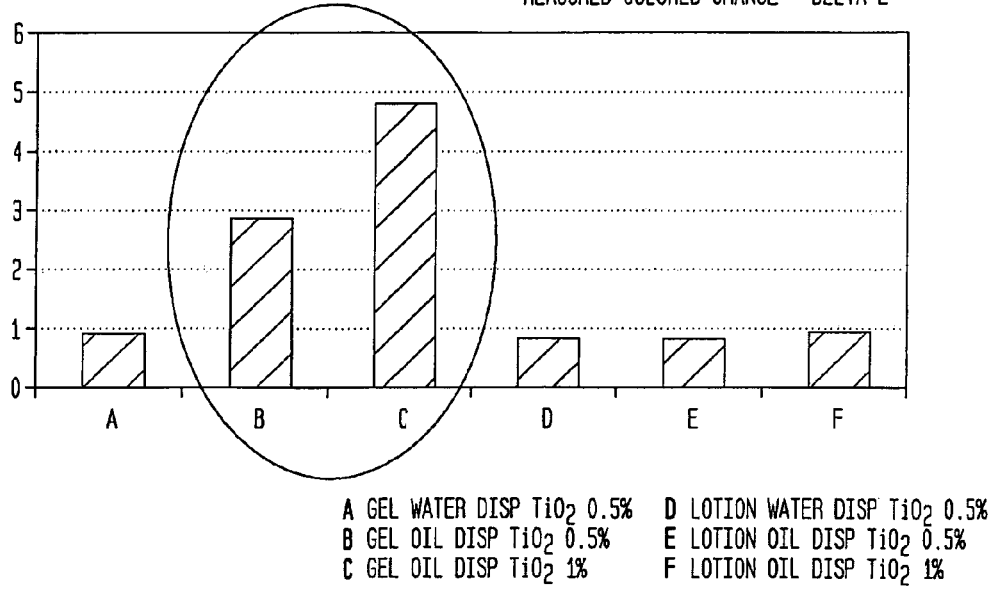

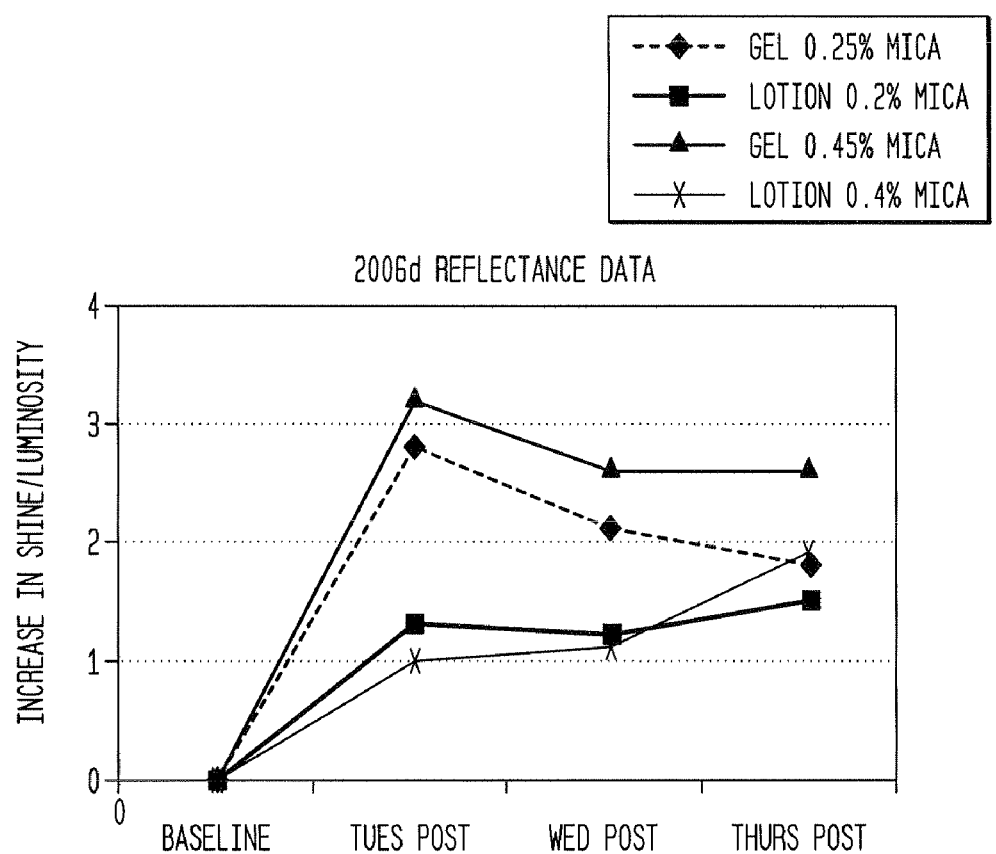

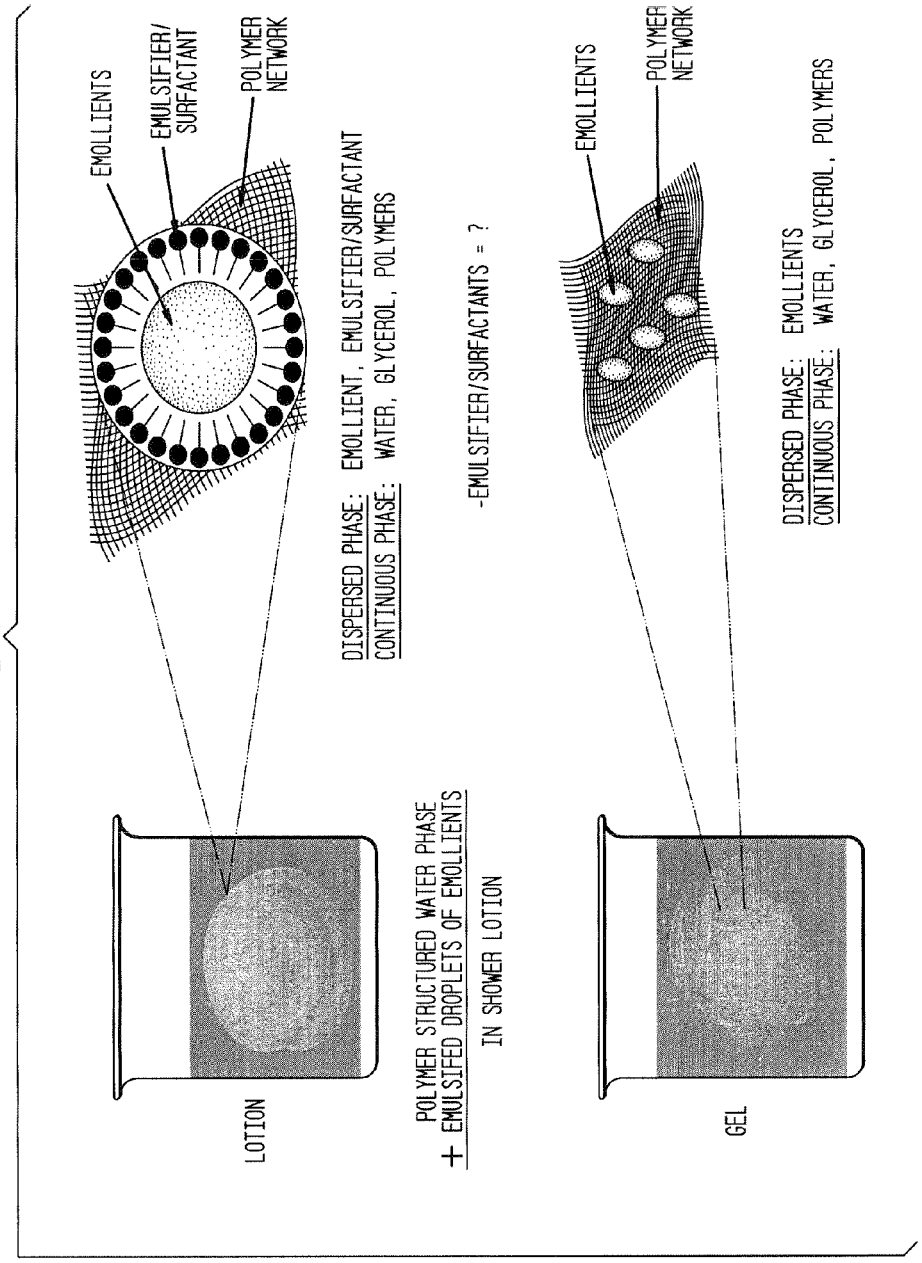

SUBSTANTIALLY SURFACTANT FREE IN-SHOWER GEL COMPOSITIONS COMPRISING HYDROPHILIC AND HYDROPHOBIC BENEFIT AGENTS

FIELD OF THE INVENTION

The present invention relates to novel compositions and to method of enhancing deposition of hydrophobic and hydrophilic agents (e.g., trichlorocarbanilide, mica, $TiO_2$) using these "gel" type in-shower lotion compositions which are substantially surfactant free. Applicants believe that, because these agents (e.g., emollients) are not emulsified, but are rather "suspended" in a structured polymer network, they are free to deposit more efficiently and hence enhance benefits associated with the deposited materials (e.g., antibacterial, whitening, luminosity, etc.).

BACKGROUND

Stable, surfactant-free liquid compositions are disclosed in, for example, U.S. application Ser. No. 11/748,943 to Patel et al. As indicated in that disclosure, use of structurants in the aqueous phase of these compositions allows preparation of stable compositions (emulsion will not separate when kept in storage at 400 for at least 2 weeks, preferably at least 50° for 3 months) without surfactant and requiring only modest levels (<14%, preferably 0.1-12%, preferably ≦10% by wt.) of hydrophobic oil/emollient (typically, higher oil levels help stabilization).

The absence of surfactant means there is no interaction between surfactant and hydrophobic phase, and permits preparation of relatively clear or transparent aqueous gels such as those disclosed in U.S. Ser. No. 11/748,943 to Patel.

Unexpectedly applicants have now found that use of the substantially surfactant free gel compositions also creates enhanced deposition of benefit agents when such agents are added to the gels.

BRIEF SUMMARY OF THE INVENTION

Thus, in one embodiment, the invention relates to gel compositions of the above-noted disclosure which additionally comprise specific hydrophobic and hydrophilic is benefit agents (e.g., trichlorocarbanilide for antimicrobial effect, mica for whitening). In a second embodiment, the application relates to a method of enhancing deposition of these materials when applying the noted gel compositions to skin or other desired substrate.

More specifically, in one embodiment the invention relates to substantially surfactant free in-shower gel compositions having enhanced deposition of benefit agents which applicants have formulated therein relative to deposition of the same agents from surfactant containing lotions. The compositions comprise greater than 60%, more preferably greater than 65%, up to 90% water and have formulation as follows:
 (1) a hydrophobic phase comprising 1 to 14%, preferably 1 to 13%, more preferably 2 to 12%, more preferably 3 to 11% by wt. (of total composition) of a hydrophobic emollient. In preferred embodiments, the emollient is an oil and said oil is petrolatum
  The hydrophobic emollient may or may not be thickened or structured; and the hydrophobic phase may optionally comprise 0 to 5%, preferably 1-4% by wt. free fatty acid; and
 (2) an aqueous phase comprising:
  (a) greater than 60%, preferably 65 to 90% by wt. water;
  (b) 5 to 25%, preferably 6 to 15% by wt. of a hydrophilic benefit agent, (especially preferred is glycerin);
  (c) 0.1 to 5%, preferably 0.1 to 3% of an aqueous phase polymer stabilizer; and
 (3) Hydrophilic and/or hydrophobic benefit agent found in aqueous phase (for hydrophilic) or in hydrophobic phase (e.g., in emollient oil). The hydrophilic is separate from the agent of 2(b) above;
wherein there is substantially no surfactant (i.e., less than 0.5%, preferably less than 0.1, preferably 0 to 0.01% by wt.).

Because of absence of surfactant (emulsifier), the benefit agents of (3) are dispersed in a polymer network rather than being emulsified and, consequently, are believed to be more available for deposition. It is believed that when hydrophobic agents are used, there is particularly good disposition because the agent can be deposited along with the hydrophobic carrier (e.g., hydrophobic emollient of (1)).

As indicated, unexpectedly, applicants have found that gel compositions comprising these additional benefit agents of (3) deposit the agent more readily than if same agents are found in in-shower surfactant-containing lotions. Thus, both compositions of the invention (comprising the benefit agent of (3)) and the method of depositing agents from these compositions are believed to be novel and unpredictably efficacious inventions.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in Si units unless specified otherwise. All documents cited are—in relevant part—incorporated herein by reference.

Figure 1A:
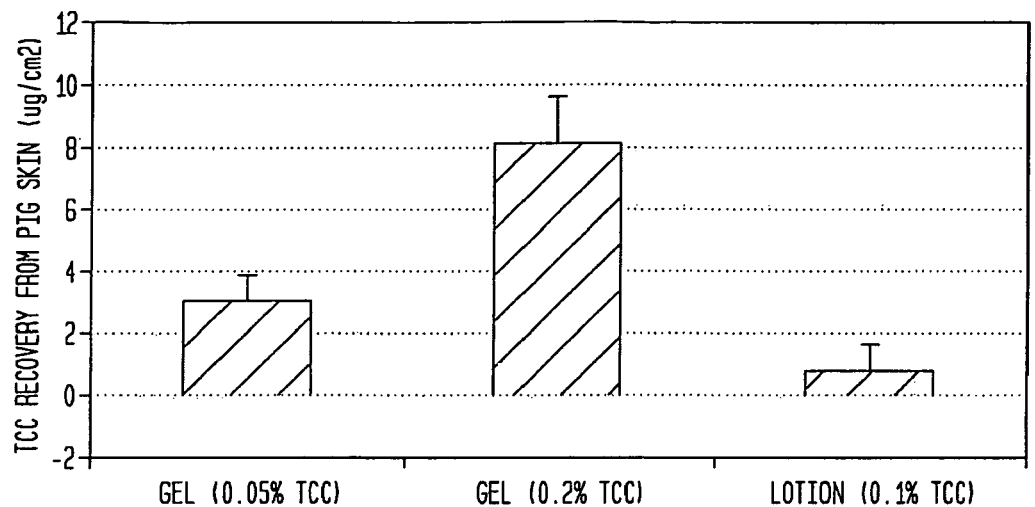
FIG. 1 (composition of Example 5) shows results of benefit agent deposition (i.e., TCC) from substantially surfactant-free in shower gel of invention. Specifically pig skin was first washed with antimicrobial free soap, and the gel of invention was subsequently applied as set forth in the protocol. Residual antibacterial (e.g., triclorocarban) was measured after rinsing to determine residual antibacterial on skin and thereby determine deposition.

As seen from FIG. 1(*a*), levels of deposition (measured by residual TCC) vary depending on whether deposition was from gel of invention or from lotion. Same results can be seen in FIG. 1(*b*).

In both cases, it can be seen that deposition of antibacterial (measured by higher residual amounts after rinsing) is superior from gels of the invention.

FIG. 2 measured (a) % of panelists who noticed whitening and (b) actual measured color change (measured by ΔE) for formulation of Example 1, i.e., gel formulation of invention when comprising 0.5% hydrophobically modified $TiO_2$ (B) or 1% $TiO_2$ (C) instead of TCC, This was compared to gel without oil dispersable $TiO_2$ (A) as well as to lotions D, E, F, and analogous to A, B & C, respectively. Lotion is the same as lotion base of Example 5, but using $TiO_2$ instead of TCC. As clearly seen, gel formulation enhanced deposition of hydrophobic $TiO_2$, as seen from whitening observations and measured ΔE results.

FIG. 3 shows results of gel of invention comprising mica versus lotion comprising mica when measuring increase in shine/luminosity (reflectance). Again, this is gel base of Example 5, but with mica added instead of TCC. The shine/luminosity was measured post wash at various points and, as seen, enhancement from gel was significantly higher.

FIG. 4 is a schematic showing how, applicants believe, difference in gel and lotion is established. The absence of emulsifier/surfactant in the gel permits emollients to not be emulsified. Thus, hydrophobic agents (which may or may not be in the emollient) can now readily deposit form emollient or polymer network; and hydrophilic agent can also more readily deposit from the polymer network.

DETAILED DESCRIPTION OF THE INVENTION

In one embodiment, the present invention relates to substantially surfactant-free in shower gel compositions comprising hydrophobic and hydrophilic benefit agents. Applicants have found that, when those agents are formulated into the substantially surfactant free gels, there is enhanced deposition or substantivity of the benefit agent (as measured, for example, by recovery of trichlorocarbanilide from pig skin).

The compositions of the invention are liquid compositions which are used, for example, in the shower and are commonly referred to as shower gel compositions.

The compositions of the invention are similar to those described in co-pending U.S. application Ser. No. 11/748,943 to Patel and, as noted therein, comprise substantially no surfactant emulsifier, yet remain stable (i.e., show no phase separation of the emollient phase from the oil-in-water emulsion after 3 months at 40° C.). The compositions of the subject invention, however, must additionally comprise the benefit agent which applicants have found deposit much better from the gels than from surfactant containing lotions.

The compositions of the invention use aqueous phase stabilizer to provide stability. As described also in the co-pending application noted above, by using aqueous phase stabilizers rather than surfactant to provide stability, there is little or no surfactant to emulsify oil in the oil phase and less oil can be used (i.e., 1 to 14%, preferably 1 to 13%, preferably 2 to 12%, more preferably 3 to 11% by wt.) to provide moisturization.

Unexpectedly what applicants have found is that these same compositions, in which there is relatively low oil and in which surfactant is substantially absent, will provide for enhanced deposition of hydrophilic and hydrophobic benefit agents, (i.e., trichlorocarbanilide, mica) compared to if the same agents had been used in surfactant-containing in-shower lotions.

By compositions having "substantially no surfactant" is meant compositions which have less than 1%, preferably less than 0.5%, preferably less than 0.2%, more preferably less than 0.1% surfactant. In some compositions, surfactant may be absent altogether. By surfactant is meant anionic, nonionic, cationic and amphoteric surfactants as are known in the art. This also includes soap surfactants.

The compositions of the invention are defined in more detail below.

Hydrophobic Phase

Emollient/Oil

The hydrophobic emollients of the invention are typically skin compatible oils by which is meant oils that are liquid at temperature at which bathing is carried out, and which are safe for use in cosmetics because they are inert to the skin or actually beneficial. Examples of such skin compatible oils include ester oils, hydrocarbon oils and silicone oils.

Ester oils as the name implies have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester, sorbitol ester, and the like.

A second type of useful esters oil is predominantly comprised of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives, provided they are liquids. Proprietary ester blends such as those sold by Finetex as Finsolv® are also suitable, as is ethylhexanoic acid glyceride.

A third type of ester oil is liquid polyester formed from the reaction of a dicarboxylic acid and a diol. An example of polyesters suitable for the present invention is the polyesters marketed by ExxonMobil under the trade name PURESYN ESTER®.

A second class of skin compatible oils suitable for the present invention is liquid hydrocarbons. These include linear and branched oils such as liquid paraffin, squalene, squalane, mineral oil, low viscosity synthetic hydrocarbons such as polyalphaolefin sold by ExxonMobil under the trade name of PureSyn PAO® and polybutene under the trade name PANALANE® or INDOPOL®. Light (low viscosity) highly branched hydrocarbon oils are also suitable.

Petrolatum is a unique hydrocarbon material and a useful component of the present invention. Since it is only partially comprised of a liquid fraction at room temperature, it may be regarded as "structured oil phase" when present by itself or alternatively as a "structurant" when admixed with other skin compatible oils.

A third class of useful skin compatible oils is silicone based. They include linear and cyclic polydimethyl siloxane, organo functional silicones (alkyl and alkyl aryl), and amino silicones. Silicones may include pre-made emulsions such as Silicone 1788® from Dow Chemical.

In one embodiment of the invention, the emollient or oil may be structured to create a structured oil phase. As indicated above, petrolatum may itself be considered a "Structured Phase".

The structurant may, for example, be either an organic or inorganic structurant. Preferred inorganic structurants are hydrophobically modified silica or hydrophobically modified clay with particle size less than 1 micrometer. Examples are Bentone 27V, Bentone 38V or Bentone gel MIO V from Rheox, and Cab-O-Sil TS720 or Cab-O-Sil M5 from Cabot Corporation.

The organic structurants are either crystalline solids or amorphous gels with molecular weight less than 5,000 Daltons, preferably less than 3,000 Daltons.

Preferred organic structurants have a melting point greater than 35° C., preferably greater than 40° C. Especially preferred structurants are those that can form a solution with the selected skin compatible oil at a temperature higher than their melting point to form a free flowing clear solution. Upon cooling to the ambient temperature, the organic structurant precipitate from the oil phase to form a 3-dimensional crystal structure providing the physical properties set forth above.

Examples of organic thickeners suitable for the invention are solid fatty acid esters, natural or modified fats, fatty acid, fatty amine, fatty alcohol, natural and synthetic waxes, and petrolatum. Petrolatum is a preferred organic structuring agents.

Particularly preferred organic structurants are solid fatty acid esters and petrolatum. Examples of solid fatty esters are mono, di or tri glycerides derivatives of palmitic acid, stearic acid, or hydroxystearic acid; sugar fatty ester or fatty esters of dextrin. Examples of these polyol fatty acid esters are described in U.S. Pat. Nos. 5,427,704, 5,472,728, 6,156,369, 5,490,995 and EP Patent 398 409 incorporated by reference herein. Trihydroxystearin sold under the trade name of THIX-CIN R from Rheox Corporation is found particularly useful for structuring triglyceride ester oils.

The level of structurant present in a structured oil phase can be in the range of 1 to 90% and depends on the type of structurant used and the nature of the skin compatible oil. For solid organic structurants such as trihydroxystearin, the preferred level is 3 to 15%. Preferably, the exact levels used should provide a stable network having the desired viscosity in the range of 100 to 5000 poise measured at a shear rate of 1 Sec-1 and can be readily optimized by one skilled in the art.

The hydrophobic emollient (e.g., oil phase), as noted above, need not be structured or thickened. This is simply one embodiment since un-thickened oils may also be used. It is surprising that un-thickened oil stays stabilized simply because of stabilizer in aqueous phase.

The emollient oil found in and/or comprising the hydrophobic phase of the invention comprises 1 to 14%, preferably 1 to 13%, more preferably 2 to 12%, more preferably 3 to 11% by wt. of the total liquid composition of the invention. In a particularly preferred embodiment of the invention, the oil comprises 3 to 7% of the composition and a preferred oil is petrolatum.

In addition the hydrophobic phase may comprise 0 to 5%, preferably 1 to 4% by wt. total composition fatty acid (e.g., saturated or unsaturated $C_{14}$-$C_{24}$ fatty acid). Preferred fatty acids include oleic acid and isostearic acid.

Aqueous Phase

Compositions of the invention also comprise an aqueous phase as noted below.

The aqueous phase typically comprise at least 60%, preferably greater than 60%, more preferably greater than 65% by wt. water.

The aqueous phase further comprises 0% to 25%, preferably 5 to 25%, preferably 7 to 20% by wt. of a hydrophilic moisturizer or skin benefit agent. Examples of such compounds are polyols such as linear and breached chain alkyl polyhydroxyl compounds. These include, for example, propylene glycol, sorbitol and glycerin.

Also polymeric polyols are useful, such as polypropylene glycol, polyethylene glycol, butylene glycol and so forth.

The aqueous phase further must comprise 0.1 to 10%, preferably 0.2 to 2.0% by wt. of a stabilizer.

Aqueous dispersion stabilizers useful in the instant invention can be organic, inorganic or polymeric stabilizers. Specifically, the compositions comprise 0.1 to 10% by wt. of an organic, inorganic or polymeric stabilizer which should provides physical stability of the oil droplets, in the composition at 37° C., 40° C. or preferably 50° C. for at least 3 months.

Inorganic dispersion stabilizers suitable for the invention includes, but are not limited to, clays, and silicas. Examples of clays include smectite clay selected from the group consisting of bentonite and hectorite and mixtures thereof. Synthetic hectorite (laponite) clay used in conjunction with an electrolyte salt capable of causing the clay to thicken (alkali and alkaline earth salts such as halides, ammonium salts and sulfates) particularly useful. Bentonite is a colloidal aluminum clay sulfate. Examples of silica include amorphous silica selected from the group consisting of fumed silica and precipitated silica and mixtures thereof.

Organic dispersion stabilizer are defined here as organic molecules that have a molecular weight generally lower than 1000 Daltons and form a network in the aqueous phase that immobilizes the dispersed oil phase. This network is comprised either of amorphous solids, crystals, or liquid crystalline phase. Suitable organic dispersion stabilizers for the instant invention are well know in the art and include, but are not limited to any of several types of long chain acyl derivatives or mixtures thereof. Included are the glycol mono- di- and triesters having about 14 to about 22 carbon atoms. Preferred glycol esters include the ethylene glycol mono- and distearates, glyceryl stearates, palm oil glyceride, tripalmitin, tristearin and mixtures thereof.

Another example of organic dispersion stabilizer are alkanolamides having from about 14 to about 22 carton atoms. Preferred alkanolamides are stearic monoethanolamide, stearic diethanolamide stearic monoisopropanolamide, stearic monoethanolamide stearate and mixtures thereof.

Still another class of useful dispersion stabilizer is long chain fatty acid esters such as stearyl stearate, stearyl palmitate, palmityl palmitate, trihydroxystearylglycerol and tristearylglycerol.

Another type of organic dispersion stabilizers is the so-called emulsifying waxes such as mixtures of cetostearyl alcohol with polysorbate 60, cetomacriogol 1000, cetrimide; a mixture of glycerol monostearate with a stearic soap, and partially neutralized stearic acid (to form a stearate gel).

Still another example of a suitable dispersion stabilizing agent is long chain amine oxides having from about 14 to about 22 carbon atoms Preferred amine oxides are hexadecyldimethylamine oxide and octadecyldimethylamide oxide.

Example of a suitable polymeric dispersion stabilizing agents useful in the present invention include: carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, carrageenan, hydroxymethyl carboxypropyl cellulose, methyl cellulose, ethyl cellulose, guar gum, gum karaya, gum tragacanth, gum arabic, gum acacia, gum agar, xanthan gum and mixtures thereof. Preferred carbohydrate gums are the cellulose gums and xanthan gum.

An especially preferred types of polymeric dispersion stabilizer agent include acrylate containing homo and copolymers. Examples include the crosslinked poly acrylates sold by B.F. Goodrich under the CARBOPOL trade name; the hydrophobically modified cross linked polyacrylates sold by B.F. Goodrich under the PEMULEN trade name; and the alkali swellable acrylic latex polymers sold by Rohm and Haas under the ARYSOL or ACULYN trade names.

The above dispersion stabilizers can be used alone or in mixtures and may be present in an amount from about 0.1 wt. % to about 10 wt. % of the composition.

Separate Benefit Agent

The next required component of our invention is hydrophobic and/or hydrophilic benefit agents, separate from the hydrophobic emollient (e.g., oil, petrolatum) or the hydrophilic moisturizing agent (e.g., glycerol) noted above.

Specifically, the agent can be a hydrophobic benefit agent (e.g., $TiO_2$ or TCC) either separately forming part of hydrophobic phase or part of other hydrophobic benefit agent. (e.g., hydrophobic particle in the petrolatum). These benefit agents (e.g., $TiO_2$ or iron oxide particles) will deposit particularly well because the petrolatum itself for example, is not emulsified and will readily deposit.

Alternatively, the agent can be a hydrophilic agent (e.g., mica) which is in the aqueous phase. Of course the mica may be hydrophobically modified and form part of hydrophobic phase or be part of hydrophobic benefit agent as noted above.

Other optionals include preservatives (e.g., parabens, sorbic acid); suds boosters (e.g., coconut acyl mono- or diethanolamide); antioxidants; cationic conditioners (e.g., Merquat® and Jaguar® type conditioners); exfoliates; ionizing salts; organic acids (e.g., citric or lactic acid).

The pH of the compositions is typically about 5.5 to 6.5, preferably 5.75 to 6.25.

Protocol for Example 5 (trichlorocarbanilide)

Stability is measured by placing product on shelf at 37° C. or 40° C., preferably at 50° C. for at least 3 months to observe whether the oil phase visually separates from the emulsion.

Deposition for Antimicrobial (e.g., for Trichlorocarbanilide or TCC).

The protocol steps are as noted below.

(a) Wash skin with antimicrobial free soap: massage 8% w/w aqueous soap slurry into a coin sized (e.g., quarter) piece pig skin using a latex gloved fingertip (product dosage—0.02 g/cm$^2$) for 1 minute; rinse by immersing the piece of pig skin in a vial containing about 10 ml water and manually shake for 5 seconds; repeat with a fresh vial of water;

(b) In-shower lotion application: without drying the piece of pig skin, apply the neat gel or lotion at a dosage of 0.02 g/cm$^2$ and massage into the skin using a gloved fingertip for 30 seconds; rinse using the protocol outlined in (a) above;

(c) TOC analysis: Allow the pig skin samples to air dry for 1 hour, then immerse in acetone for 1 hour to extract deposited TCC; analyze for TCC by high performance liquid chromatography (HPLC).

CONTROL AND EXAMPLES 1-4

The following Examples 1-4 are examples of the gels of the invention

| Function | | Gel Base Control | Example 1 (Whitening SPF) | Example 2 (Luminosity) | Example 3 (Tanning/ Bronzing) | Example 4 (anti- microbial) |
|---|---|---|---|---|---|---|
| Polymer | Ultrez 21 | 0.30% | 0.30% | 0.30% | 0.30% | 0.30% |
| Emollients | Glycerine | 10.00% | 10.00% | 10.00% | 10.00% | 10.00% |
| | Petrolatum | 5.00% | 5.00% | 5.00% | 5.00% | 5.00% |
| | Fatty Acid (oleic acid/Isostearic acid) | 3.00% | 3.00% | 3.00% | 3.00% | 3.00% |
| Preservatives | Liquapar MEP | 0.75% | 0.75% | 0.75% | 0.75% | 0.75% |
| | Versene 100 XL | 0.050% | 0.050% | 0.050% | 0.050% | 0.050% |
| pH Adjust | Sodium Hydroxide | 0.13% | 0.13% | 0.13% | 0.13% | 0.13% |
| Actives | Hydrophobically Modified $TiO_2$ | | 0.1-2% | | | |
| | Mica | | | 0.1-2% | | |
| | Iron Oxide | | | | 0-2% | |
| | TCC | | | | | 0.1-1% |

EXAMPLE 5

Improved Antibacterial Results Using Gel

Example of both base lotion (comparative) and gel (where enhanced deposition of AB occurs) are set forth below:

In-Shower Liquids (ISLs)

| | Lotion base + 0.1% TCC | Gel base + 0.05, 0.2% or 1.0% TCC |
|---|---|---|
| Polymers & Emulsifiers | | |
| Acrylate C10-12 Alkyl Acrylates Crosspolymer | 0.263% | |
| Acrylates C10/30 Alkyl Acrylate Crosspolymer | 0.15% | 0.30% |
| Xanthan Gum | 0.15% | |
| Decyl Glucoside | 0.95% | |
| Emollients | | |
| Glycerin | 10.00% | 10.00% |
| Petrolatum (G2212) | 7.50% | |
| Petrolatum Liquid | | 5.00% |
| Caprylic/Capric Triglycerides | 0.70% | |
| Octyldodecanol | 0.25% | |
| Hydrogenated Polydecene | 0.25% | |
| Soybean (or Sunflower) oil | 2.50% | |
| Lauric Acid | 0.50% | |
| Oleic Acid | 0.50% | 3.00% |
| Water | To 100% | To 100% |

As seen from FIG. 1, when antibacterial is in the gel of invention, there is superior deposition. This is seen from residual TCC after rinsing, as it can be seen that 0.05% TCG deposited about 3 times amount (3 μg/cm$^2$ versus 1 μg/cm$^2$) as the lotion at 0.1% TCC. At 0.2% TCO, recovery was at about 8 μg/cm$^2$.

Figure 1B:
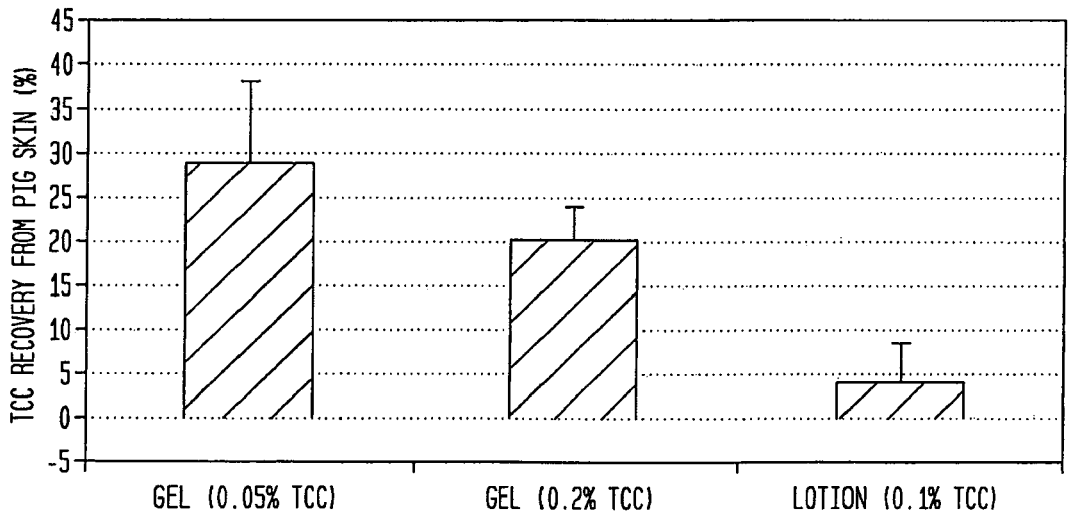

In FIG. 1(b), again it can be seen that percent recovery is much higher when using gel versus lotion.

EXAMPLE 6

Improved Whitening Using Gel

In Example 6, applicant used either 0.5% or 1% $TiO_2$ in gel composition of invention with oil. The gel and lotion compositions were substantially the same as used in Example 5. The gel compositions of the invention are samples B & C (Example A was gel water dispersion). The lotion compositions are samples D, E & F. Again, whether % of panelists noticing whiteness or measured color change, using $\Delta E$, the results can be clearly observed in FIGS. 2(a) and 2(b).

A more detailed summary of the example and protocol is as follows:

The $TiO_2$ study was to determine (1) % of panelists noticing whiteness; and (2) color change, measured using $\Delta E$ results.

For purposes of this test, panelists measured whiteness by self assessment and $\Delta E$ was measured using a chromameter.

Specifically for each panelist, six sites on each panelists' forearms were washed (one area was untreated) with each product. Base line measurements were with the chromameter before product application. Also, standard prewash was performed with Dove® white bar. 0.5 ml of product was applied to the set test area and rubbed for about 30 seconds. The test site was rinsed for 15 seconds and allowed to dry. Chromameter readings and self assessment were taken 10 minutes after the wash. In a typical panel, 31 female panelists, about ages 20-51 were selected.

As indicated chromameter readings were taken both at baseline and about 10 minutes after wash and self assessments were taken 10 minutes after the wash. Delta E is calculated from chromameter readings and significance between Delta E values was set at p<0.05.

As seen from results in FIG. 2(a), based on self assessment results, 95-100% of the panelists clearly noted whitening after treatment with gel comprising $TiO_2$ when delivered as gel oil dispersion (samples B & C). These results were confirmed using measured $\Delta E$ results.

EXAMPLE 7

Improved Shimmer and Shine (e.g., Luminosity or Reflectance) Using Gel

In Example 7, applicants sought to show improvements wherein, for example, mica was deposited from a gel versus a lotion. Again, gel and lotion compositions were substantially similar to those used in Example 5, except for use of mica instead of TCC.

More specifically, the gel and lotion of this example comprises as follows:

| Ingredient | Lotion % | Gel % |
|---|---|---|
| Acrylate $C_{10-12}$ aklyl acrylates crosspolymer | 0.263 | |
| Acrylate $C_{10}/C_{30}$ aklyl acrylate cross-polymer | 0.15 | .30 |
| Xanthan gum | 0.15 | |
| Decyl glucoside | 0.95 | |
| Glycerin | 10.00 | 10.00 |
| Petrolatum | 7.5 | |
| Petrolatum liquid | | 5.00 |
| Caprylic/Capric Triglycerides | 0.70 | |
| Octyldodecanol | 0.25 | |
| Hydrogenated Polydecene | 0.25 | |
| Sunflower oil | 2.5 | |
| Lauric acid | 0.5 | |
| Oleic acid | 0.5 | 3.00 |
| Mica | 04 | 0.25 |
| Water, preservatives, colorants, perfume | 60.45 | 79.25 |

According to the test, baseline measurements with a spectrophotometer 2600d were taken and self assessment completed before product application. Four sites on each panelists' forearm were washed with each product. Sites were allowed to dry (about 20 minutes) and spectrophotometer readings taken. Reflectance visual gradings of shine were performed and self-assessment completed. This was repeated for four (4) days.

Reflectance was obtained from measurements taken from the spectrophotometer. Two readings were taken from each site and averaged. Panelists were also asked to evaluate glow/shine and shimmer on a 5-point scale.

Specifically, reflectance was calculated for each measurement by summing values for SCE and SCI across each wavelength and subtracting SCE (specular component excluded) from SCI (specular component included). The values for the two measurements at each site were then averaged. Change from baseline, area under curve and significance were then determined. Visual grading data was averaged at each timepoint and compared to the ideal amount of shine.

The results for reflectance are noted in the table below.

| | Baseline | Tues Post Wash | Wed Post Wash | Thurs Post Wash | AUC |
|---|---|---|---|---|---|
| Gel w/0.25 mica | 0.0 | 2.8 | 2.1 | 1.8 | 5.8 |
| Lotion w/0.4 mica | 0.0 | 1.0 | 1.1 | 1.9 | 3.1 |

R-Values Resulting from Ttest Comparisons

| | Lotion 0.2% Mica | Gel 0.45% Mica | Lotion 0.4% Mica |
|---|---|---|---|
| Gel 0.25% Mica | 0.013* | 0.271 | 0.007* |
| Lotion 0.2% Mica | | 0.001* | 0.871 |
| Gel 0.45% Mica | | | 0.003* |

*Indicate a significant p-value (<0.05)

As seen from the Table and charted on FIG. 3, significant enhancement in shine/luminosity (reflectance) is seen when using gel versus lotion.

EXAMPLE 8

Improved Bronzing

Again using substantially similar composition of Example 5, but substituting 0.5 iron oxide for TCC, applicants saw enhanced bronzing effect when the iron oxide was deposited from gel compared to if no iron oxide was deposited from gel.

The invention claimed is:

1. A gel composition for enhancing deposition of hydrophilic and/or hydrophobic benefit agent comprising >60% water and additionally having formulation as follows:
   (a) a hydrophobic phase comprising 1 to 14% by wt. (of total composition) petrolatum and 1 to 4% by wt. $C_{14}$ to $C_{24}$ fatty acid;
   (b) an aqueous phase consisting of:
      (i) greater than 60% by wt. water;
      (ii) 5 to 25% of a hydrophilic moisturizing agent;
      (iii) 0.1 to 5%, of an aqueous phase stabilizer; and
   (c) 0.01-3% by wt. hydrophilic and/or hydrophobic benefit agents separate from hydrophilic agent of (b)(ii) or the hydrophobic agent of (a);
   wherein there is 0.5 or less surfactant;
   wherein said gel is clear or transparent.

2. A composition according to claim 1, wherein said petrolatum is structured.

3. A composition according to claim 1, wherein hydrophobic phase comprises 1-13% by wt. petrolatum.

4. A composition according to claim 1, wherein aqueous phase comprises 65-90% water.

5. A composition according to claim 1, wherein aqueous phase comprises 6-15% hydrophilic benefit agent (b)(ii).

6. A composition according to claim 5, wherein hydrophilic benefit agent is glycerin.

7. A composition according to claim 1 wherein additional hydrophobic benefit agent of (3) is TCC.

8. A composition according to claim 1 wherein additional hydrophobic benefit agent of (3) is $TiO_2$.

9. A composition according to claim 1 wherein additional hydrophobic or hydrophilic benefit agent of (3) is mica.

10. A composition according to claim 9 wherein said hydrophobic mica is hydrophobically modified mica.

11. A composition according to claim 1 wherein there is 0.1% by wt. or less surfactant.

* * * * *